United States Patent [19]

Wachi et al.

[11] Patent Number: 4,774,372

[45] Date of Patent: Sep. 27, 1988

[54] METHOD FOR PRODUCING DICHLOROETHANE

[75] Inventors: Shun Wachi; Yuusaku Ariki, both of Takasago, Japan

[73] Assignee: Kanegafuchi Kagaku Kogyo Kabushiki Kaisha, Osaka, Japan

[21] Appl. No.: 84,245

[22] Filed: Aug. 12, 1987

Related U.S. Application Data

[63] Continuation-in-part of Ser. No. 830,801, Feb. 19, 1986.

[30] Foreign Application Priority Data

Feb. 19, 1985 [JP] Japan ................................ 60-31261

[51] Int. Cl.[4] ...................... C07C 17/02; C07C 19/045
[52] U.S. Cl. .................................... 570/247; 570/246
[58] Field of Search ................. 570/247, 252, 253, 246

[56] References Cited

U.S. PATENT DOCUMENTS

| | | | |
|---|---|---|---|
| 2,403,977 | 7/1946 | Heard | 570/247 |
| 3,839,475 | 10/1974 | Kurtz et al. | 570/247 |
| 3,911,036 | 10/1975 | Di Fiore et al. | 570/247 |
| 4,347,391 | 8/1982 | Campbell | 570/252 |
| 4,672,142 | 6/1987 | Hundeck et al. | 570/247 |

FOREIGN PATENT DOCUMENTS 2119802 11/1983 United Kingdom .

OTHER PUBLICATIONS

Wachi et al., Kagaku Kogaku Ronbunshu, vol. 13, No. 2, pp. 230–233, Mar. 1987.

Primary Examiner—J. E. Evans
Attorney, Agent, or Firm—Armstrong, Nikaido, Marmelstein & Kubovcik

[57] ABSTRACT

A method for producing dichloroethane (EDC) from ethylene and chlorine in high selectivity, yield and efficiency and in high safety wherein the unreacted ethylene and oxygen included in an exhaust gas discharged from a reactor are prevented from forming an explosive gas mixture by diluting the exhaust gas with a dichloroethane vapor.

8 Claims, 3 Drawing Sheets

METHOD FOR PRODUCING DICHLOROETHANE

CROSS-REFERENCE TO RELATED APPLICATION

This is a continuation-in-part of application Ser. No. 830,801 filed on Feb. 19, 1986 pending.

BACKGROUND OF THE INVENTION

The present invention relates to a method of producing dichloroethane (ethylene dichloride) (hereinafter referred to as "EDC") by reacting ethylene and chlorine in a liquid reaction medium. More particularly, the invention relates to a method of producing EDC in a high selectivity and a high efficiency with preventing the discharge gas from the reactor from forming an explosive mixture.

EDC is industrially important as a starting material in the production of vinyl chloride monomer. Various methods for producing EDC and improvements thereof have hitherto been proposed, for instance, as disclosed in U.S. Pat. No. 2,929,852, British Pat. No. 1,184,576, Japanese Patent Publication Kokai No. 57906/1973 and Japanese Patent Publication Kokai No. 177923/1983. In the production of EDC by direct chlorination, ethylene and chlorine are fed to the reaction system, and when ethylene is fed in a stoichiometrically excess amount, the unreacted ethylene is discharged.

Chlorine to be fed to a reactor has been produced by the mercury process. In recent years, in view of prevention of mercury pollution, the production of chlorine is being switched from the mercury process to the diaphragm process as an industrial chlorine production process not using mercury. This switching of the process has greatly altered the quality of chlorine gas. Oxygen gas included in the chlorine gas produced by the mercury process mainly results from incorporation of air, and the oxygen concentration is at most about 0.5%. In contrast, the chlorine gas produced by the diaphragm process contains about 1 to 5% of oxygen.

In another aspect, as disclosed in Japanese Patent Publication Kokai No. 177923/1983, it is known that addition of oxygen is preferable for efficiently producing EDC. In the production of EDC by addition reaction of ethylene and chlorine, trichloroethane is by-produced by chlorine substitution reaction to thereby lower the reaction yield. Oxygen can depress this side reaction. Therefore, even in the case where the amount of oxygen included in the fed chlorine gas is small, oxygen may be utilized in an amount up to about 10% based on the amount of fed chlorine by adding oxygen gas in view of the reaction yield.

The reaction of ethylene and chlorine to produce EDC is accompanied by heat generation of about 50 kcal/mole. In the past, the reaction was conducted at about 50° C. with cooling with water or the like. Since a method which utilizes the heat of reaction efficiently was proposed in U.S. Pat. No. 2,929,852, there has been widely practiced a so-called high temperature method wherein ethylene is reacted with chlorine at a temperature not lower than 83° C. by feeding the reactants into a liquid reaction medium composed mainly of EDC. In accordance with the method proposed in the above U.S. patent, a reaction-distillation scheme is adopted, namely the liquid reaction medium is vaporized by the heat of reaction and the vapor generated is introduced for purification into a distillation column connected with the upper part of the reactor, so that the heat of reaction can be efficiently utilized as a source of energy required for purification of EDC.

In the high temperature method, it is particularly effective to use oxygen in order to prevent by-production of trichloroethane by chlorine substitution side reaction, as disclosed in Japanese Patent Publication Kokai. No. 177923/1983. Also, in the high temperature method, for keeping the selectivity of reaction on a high level, it is effective to use ethylene in excess, as proposed in British Pat. No. 1,184,576. When ethylene is used in excess, unreacted ethylene is discharged. Therefore, it is important to recover the unreacted ethylene discharged. However, increase of the discharged unreacted ethylene to be treated for recovery in a second reactor decreases the utilization efficiency of the heat of reaction in the main reactor.

When chlorine gas containing a large amount of oxygen is fed to a reactor, most of the chlorine is consumed for the reaction, then oxygen is concentrated at a flow passage of exhaust gas discharged from the reactor, or at other places. Therefore, the risk that the discharge gas containing a high concentration of oxygen gas and an inflammable gas such as ethylene forms an explosive gas (detonating gas), greatly increases.

One of the safety measures which have hitherto been taken to counter the problem of explosion risk, is a method wherein a mixed gas is diluted by introducing an inert gas such as nitrogen to a flow passage where oxygen in the discharge gas from the reactor is concentrated, thereby avoiding formation of a detonating gas. However, this method has the disadvantages that a large amount of inert gas must be introduced for dilution and that it is difficult to recover ethylene included in the discharge gas, because of lowering of the ethylene concentration of the discharge gas to be fed to a second reactor for recovery.

As another safety measure, it is proposed, for instance, in Japanese Patent Publication Kokai Nos. 105603/1975 and 105604/1975 and Japanese Patent Publication Kokoku No. 6926/1985, to avoid formation of a detonating gas by adding ethylene to the discharge gas or by controlling the amount of ethylene to be fed to the reactor so as to raise the ethylene concentration of the discharge gas. This method has the disadvantages that it is necessary to discharge an amount of ethylene sufficient to avoid formation of an explosive mixture in the unreacted state in accordance with the amount of oxygen utilized for the reaction, thus usually ethylene must be recovered using a second reactor or the like, and that when the amount of oxygen is relatively large, the load on the second reactor becomes large relative to the main reactor.

It is an object of the present invention to eliminate the disadvantages of the conventional techniques applied to avoid formation of an explosive gas mixture in a passage of the discharge gas from a reactor for the production of EDC from ethylene and chlorine.

A further object of the present invention is to provide a process for producing EDC from ethylene and chlorine in high selectivity, yield and efficiency, wherein an explosive gas mixture is prevented from being formed in a passage of the discharge gas from a main reactor for the reaction of ethylene and chlorine, while in order to maintain the selectivity on a high level a relatively large amount of oxygen is utilized and an excess amount of ethylene is maintained on a proper level.

These and other objects of the present invention will become apparent from the description hereinafter.

SUMMARY OF THE INVENTION

It has now been found that a ternary mixed gas of ethylene, EDC and oxygen forms an explosive gas mixture as shown in FIG. 2, and that when EDC vapor is used as a third component for preventing the unreacted ethylene and oxygen from forming an explosive gas, the safety region is very wide, thus EDC can be advantageously produced with securing the safety based on the explosion and safety regions of a ternary mixed gas of ethylene, EDC and oxygen.

In accordance with the present invention, there is provided a method for producing dichloroethane which comprises reacting ethylene and chlorine in a liquid reaction medium containing dichloroethane as a main component in a first reactor, recovering the reaction product in the form of liquid, leading the discharge containing an unreacted component from the first reactor to a second reactor in the form of gas, and diluting the discharge gas containing the unreacted ethylene and oxygen in a molar ratio of 3:97 to 90:10 with a dichloroethane vapor so that the content of dichloroethane in the resulting mixture is at least 15% by mole, thereby preventing the unreacted ethylene and oxygen from forming an explosive gas mixture.

DETAILED DESCRIPTION

The reactor used in the method of the invention may be of various types, e.g. reactors of the tower type, of the vessel type or further of the loop- or double pipe-shaped liquid circulation type. The so-called low-temperature method and high-temperature method are applicable to the reaction of ethylene and chlorine. The reactor is charged with a liquid reaction medium which contains EDC (dichloroethane) as the main component, and thereto are fed ethylene and chlorine. Ethylene and chlorine are preferably fed in amounts such that ethylene is stoichiometrically in excess. The ethylene/chlorine molar ratio is selected from 1.01 to 1.20 so as to minimize the unreacted chlorine. When the amount of the unreacted chlorine is large, corrosion of materials in the following steps may occur. In particular, in case of conducting the reaction according to the high temperature method, the unreacted chlorine increases by-production of trichloroethane and, therefore, it is rather preferred to feed ethylene in excess. Iron chloride or known other catalytically active substances may be used as catalysts for the reaction.

Oxygen is effective for preventing by-production of trichloroethane owing to chlorine substitution reaction, thus raising the selectivity of reaction. Oxygen can be fed to the reactor in an amount of 0.01 to 0.1 mole per mole of chlorine fed. The oxygen fed to the reactor may be oxygen originally included in the chlorine fed as a raw material or may be additionally fed to the reactor from another source. Oxygen is usually fed in admixture with chlorine, but it may be fed separately to the reactor.

EDC produced in the first reactor is recovered as the product from the reactor in the form of liquid. In the case where EDC is taken out from the reactor in the form of vapor, it is condensed and finally recovered as the liquid product, and an exhaust gas such as unreacted components is discharged through another passage separately from the liquid EDC product. The ethylene/oxygen mixing ratio in the discharge passage varies depending on the excess amount of ethylene and the amount of oxygen fed, but usually is from 3/97 to 90/10 by mole.

Figure 2:
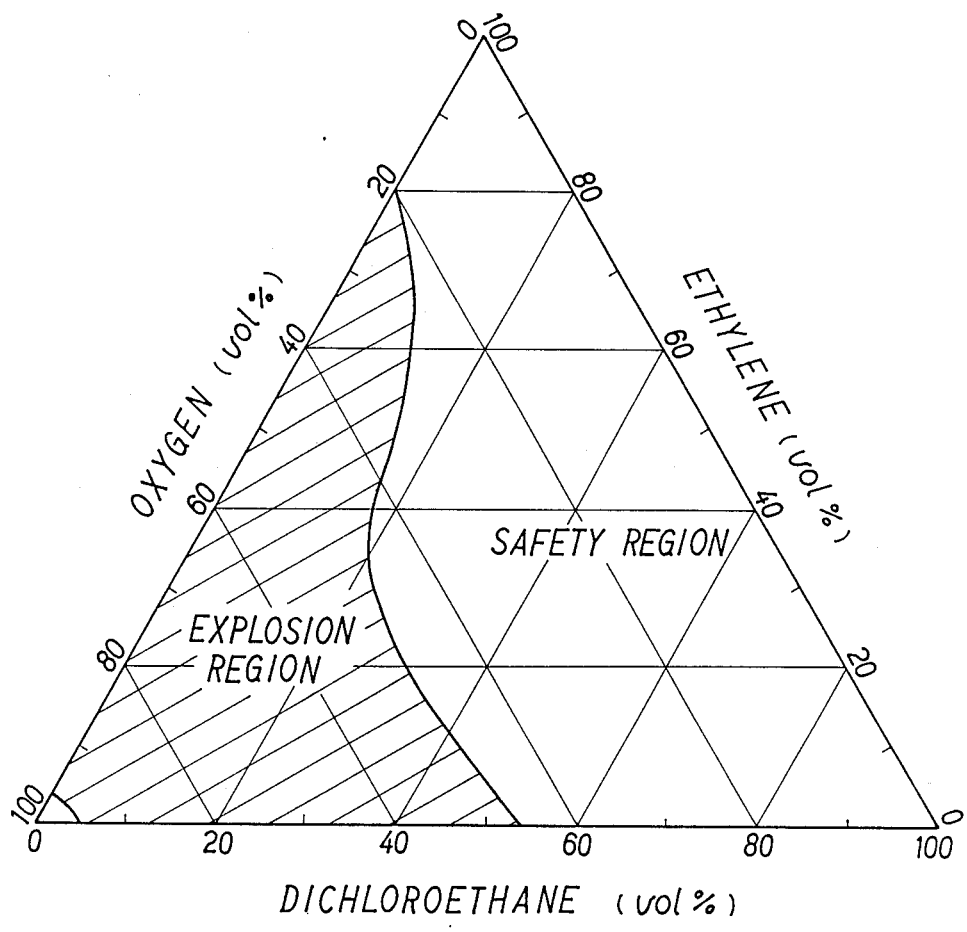
FIG. 2 is a triangular diagram illustrating the explosion region of a ternary mixture of ethylene, oxygen and EDC.

The most characteristic feature of the present invention resides in that in order to prevent the unreacted ethylene and oxygen in the discharge passage from forming an explosive mixture, the exhaust gas is admixed with an EDC vapor so that the composition of the ternary mixture of ethylene, EDC and oxygen falls within the safety region shown in the triangular diagram of FIG. 2. From the viewpoint of operational easiness, it is convenient to admix the exhaust gas with an EDC vapor so that the EDC content in the resulting mixed gas is at least 15% by weight.

More surely, the safety against explosion can be secured by introducing the EDC vapor in an amount such that the content of oxygen in the resulting mixed gas is not more than 40% by mole and the oxygen/EDC ratio is not more than 3/2 by mole. When the EDC vapor is introduced so that the resulting mixed gas contains not less than 60% by mole of EDC, oxygen and ethylene can be present in all proportions.

The composition of the mixed gas can be adjusted, for instance, in a manner such that the amount of oxygen fed to the reactor and the amount of the excess of ethylene are determined by measuring the feed amounts, and the amount of EDC vapor required is determined on the basis of the presumed amounts of ethylene and oxygen in the exhaust gas, or in a manner such that the composition of the exhaust gas is analyzed and the amount of EDC vapor to be admixed is controlled so as to give a proper concentration.

The EDC vapor to be admixed with the exhaust gas may be obtained from any sources.

For instance, EDC produced in the reactor can be utilized for the dilution. The obtained liquid EDC contains impurities such as unreacted components, by-products and catalysts. Low-boiling substances among these impurities can be readily removed by distillation which can be attained by a relatively small heat energy. In an embodiment, the produced liquid EDC is drawn out from the reactor and is fed to a distillation column where low-boiling impurities are separated and drawn out from the column top. The column top vapor is then introduced to the discharge passage through which the exhaust gas is discharged from the reactor. The low-boiling impurities can be concentrated in a vapor at the top of the distillation column by a relatively small heat energy. Therefore, the introduction of the column top vapor to the discharge passage is preferable, since the unreacted components are also introduced to the discharge gas passage simultaneously with the low-boiling impurities accompanied by EDC vapor. The vapor from the distillation column top to be introduced into the reactor discharge gas may be the whole or a part of it.

In another embodiment, the reaction in the first reactor is carried out by the so-called high temperature method, and a part of the generated reaction medium vapor containing the produced EDC is maintained in the uncondensed state and discharged together with the exhaust gas through the discharge gas passage. The reaction of ethylene and chlorine is accompanied by heat generation of about 50 kcal/mole. In the high temperature method, the reaction is conducted in the liquid reaction medium containing EDC in a major amount, and the reaction medium is boiled and vaporized by the heat of reaction. Since the heat of reaction is about 7 times the quantity of heat required for vaporizing the EDC produced by the reaction of ethylene and chlorine, the generated reaction medium vapor composed mainly of EDC vapor is condensed to liquefy in a condenser and a large portion of the condensate liquid is returned to the reactor in order to maintain the quantity of reaction medium constant. At that time, a portion corresponding to the produced EDC is drawn out as the product EDC. It is desirable to take out the produced EDC mainly as the product, but by maintaining a part of the EDC vapor uncondensed and leading to the discharge gas passage to dilute the discharge gas, it is possible to avoid formation of an explosive gas mixture.

The amount of the reaction medium vapor to be maintained in the uncondensed state is selected from 0.05 to 1.0 time the number of moles of chlorine fed to the first reactor. Upon maintaining a part of the EDC vapor uncondensed for the dilution of exhaust gas, a heat exchanger is installed on or over the top of the reactor, and the generated reaction medium vapor is cooled to liquefy EDC in the heat exchanger where the temperature of a cooling medium on the heat receiving side is maintained at a temperature of not less than 80° C. to secure a predetermined amount of the uncondensed vapor.

The heat exchanger can be selected from known heat exchangers, e.g. shell-and-tube heat exchanger of thermosiphon type, kettle type or falling film type, in consideration of the heat transfer coefficient of the heat receiving side, scale adhesion, site area, cleaning method and so on.

Since the temperature of the heat receiving side of the heat exchanger is relatively high under the above conditions, it is possible to effectively utilize the heat of condensation of the EDC vapor. For instance, when the heat receiving side of the heat exchanger is used as a reboiler of a distillation column for purifying EDC, the heat energy which has been used for operating the distillation column can be saved. Further, it is also possible to utilize the heat of condensation as energy sources for temperature elevation of hot water, heat medium or the like, evaporation, drying, etc.

On the other hand, when the reaction medium vapor from the reactor top is cooled to liquefy in a heat exchanger at a temperature as low as about 20° to about 60° C. by using a cooling water on the heat receiving side, not only it is difficult to recover and utilize the heat, but also there is a risk of lack of the uncondensed vapor to be introduced to the discharge gas passage because a large portion of EDC vapor is liquefied.

The EDC vapor obtained by other means is also usable for the dilution of discharge gas.

The discharge gas diluted according to the present invention contains ethylene and EDC as effective components. Accordingly, in case of recovering them, a second reactor can be used. For instance, a reactor wherein liquid EDC is used as a reaction medium and the temperature and pressure are maintained at 40° to 60° C. and 1 to 2 kg/cm² G (gauge pressure), is used as the second reactor. The exhaust gas from the first reactor is fed to the second reactor where the ethylene included in the exhaust gas is reacted with chlorine separately fed, while a large portion of the EDC vapor included in the exhaust gas is condensed to liquefy in the reaction medium.

Figure 3:
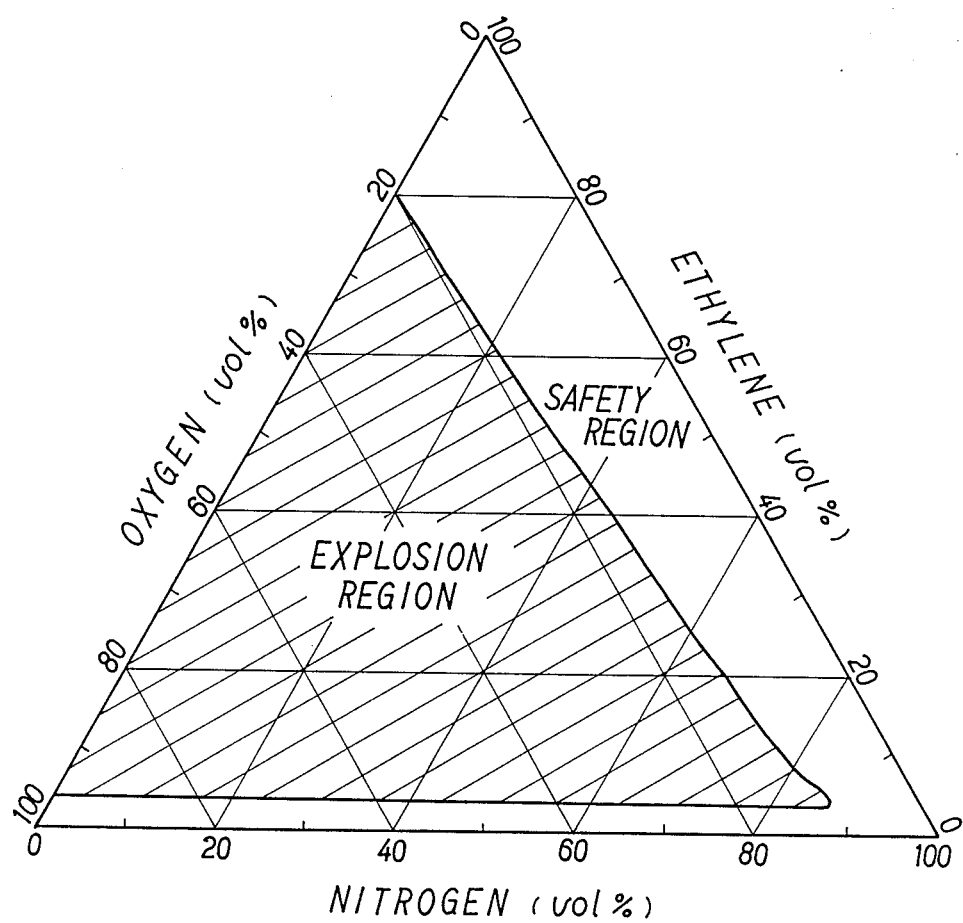
FIG. 3 is a triangular diagram illustrating the explosion region of a ternary mixture of ethylene, oxygen and nitrogen.

According to the method of the present invention, advantages as mentioned below can be obtained. In addition to the fact that a favorable amount of oxygen can be used in order to maintain the selectivity of reaction high, the method can be practiced safely without feeding of a large excess of ethylene to the main reactor which makes the load on the second reactor higher than the load on the main reactor. Also, as compared with a conventional method where a discharge gas from the main reactor is diluted with an inert gas such as nitrogen in order to avoid formation of an explosive mixture, the method of the invention is advantageous in that formation of an explosive mixture can be easily avoided because of a broader safety region and that the quantity of the discharge gas so adjusted is small. FIG. 2 shows the explosion region of a ternary mixture of ethylene, oxygen and EDC, and FIG. 3 shows the explosion region of a ternary mixture of ethylene, oxygen and nitrogen. As apparent therefrom, the safety region of the ethylene/oxygen/EDC mixture is broader. Further, when the unreacted ethylene is recovered by introducing the discharge gas into a second reactor, the method of the invention is advantageous in that the EDC vapor is readily condensed in the second reactor and, therefore, a relatively high concentration of the unreacted ethylene gas can be absorbed, as compared with a conventional method where the ethylene concentration is lowered by dilution of the discharge gas with nitrogen. Also, in a conventional method where the formation of an explosive mixture is avoided by including a large excess of unreacted ethylene in the discharge gas, ethylene discharged in the unreacted state in a large amount from the reactor must be increased with increase of the amount of oxygen, thus the amount of ethylene to be treated in the second reactor becomes larger than that in the main reactor, but it can be minimized according to the method of the invention.

The present invention is more specifically described and explained by means of the following Examples. It is to be understood that the present invention is not limited to the Examples, and various changes and modifications may be made in the invention without departing from the spirit and scope thereof.

EXAMPLE 1

Figure 1:
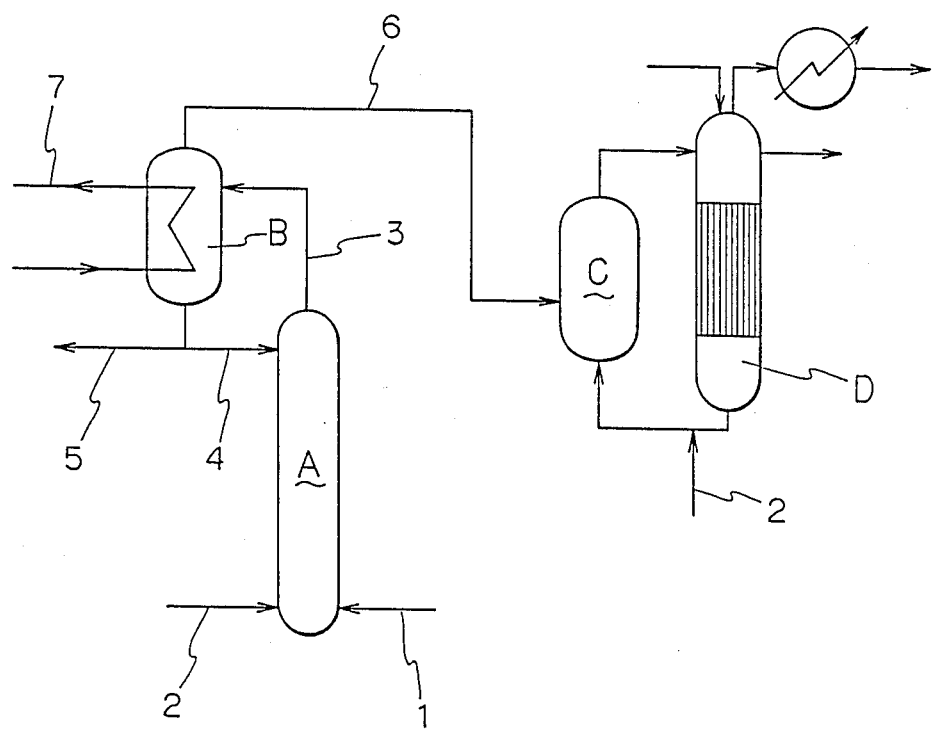
FIG. 1 is a flow diagram showing an embodiment of an EDC manufacturing apparatus used for practicing the process of the present invention.

EDC was produced by using the apparatus shown in FIG. 1. First reactor A was charged with EDC liquid and about 1,500 wt. ppm of ferric chloride was dissolved therein as a catalyst. Chlorine was fed from conduit line 2 at a rate of 700 kg/hr, while ethylene was fed from conduit line 1 at a rate of 287 kg/hr, and the reaction was conducted at about 2% by mole excess of ethylene. The chlorine contained 2% by mole of oxygen. With the reactor column top pressure maintained at 4 atm, the liquid reaction medium was boiled at 135° C. to maintain the temperature constant. The vapor of the reaction medium gasified by the heat of reaction was fed to heat exchanger B through the conduit line 3. The condensation temperature in the heat exchanger B was controlled at 124° C. by adjusting heat medium 7. A portion of the condensate was withdrawn as a product through conduit 5, while the remainder was returned to the reactor A through conduit 4. The vapor pressure of EDC at 124° C. was about 3.08 atm, which was about 75% of the total pressure. The components drawn as uncondensed gas from conduit 6 to feed to second reactor C were about 4,400 Nl/hr of oxygen, about 4,400 Nl/hr of ethylene, about 33,200 Nl/hr of EDC and about 2,000 Nl/hr of other components. Since this composition was within the safety region indicated in FIG. 2, it was not explosive. The total amount of gas flowing through the conduit 6 was measured and the condensation temperature was adjusted to ensure an appropriate flow rate. The second reactor C charged with EDC and connected to an external heat changer D was maintained at 60° C. The fraction from the conduit 6 was fed to the reactor C and reacted with chlorine from conduit line 2, the amount of chlorine fed corresponding to the amount of unreacted ethylene. In this stage, the load on the first reactor was about 98% of the total load, and the heat of reaction in the first reactor was recovered by the heat medium 7 of the heat exchanger B for re-use. The load on the second reactor was about 2% of the total load, and the ethylene concentration after liquefaction of EDC was about 45%, thus recovery by absorption was quite easy. The total volume of discharge gas was about 44,000 Nl/hr. The heat of reaction was efficiently recovered to the amount of 98%.

EXAMPLE 2

The reaction was conducted in the same manner as in Example 1 except that ethylene was fed at 290 kg/hr, the ethylene excess being about 3%, and the oxygen content in chlorine was 2%. When the reaction temperature and the condensation temperature were maintained at 135° C. and 100° C., respectively, the components discharged as uncondensed gases from the conduit 6 were about 4,400 Nl/hr of oxygen, about 17,600 Nl/hr of ethylene, about 16,200 Nl/hr of EDC, and about 2,000 Nl/hr of others. This composition was within the safety region shown in FIG. 2.

The volume of discharge gas under the above conditions was about 40,000 Nl/hr. Compared with the first reactor, the ethylene loading for the second reactor C was as low as about 8% and the ethylene concentration liquefaction of EDC was as high as about 75%. Therefore, recovery by absorption was easy. The heat of reaction was efficiently recovered to the amount of 92%.

EXAMPLE 3

The reaction was conducted in the same manner as in Example 1 except that chlorine was fed at 200 kg/hr, the oxygen content in the chlorine was 3%, and ethylene was fed at a rate of 80 kg/hr with an excess of about 1%. When the reaction temperature and the condensation temperature were maintained at 110° C. and 97° C., respectively, the EDC vapor pressure at this condensation temperature was 1.50 atm against the total pressure of 2.16 atm. The components discharged as uncondensed gases from the conduit 6 were about 1,900 Nl/hr of oxygen, about 630 Nl/hr of ethylene, about 6,100 Nl/hr of EDC, and about 100 Nl/hr of other gases. Thus, this composition was within the safety region shown in FIG. 2.

In this operation, the volume of the discharge gas was about 8,700 Nl/hr. The ethylene load on the first reactor was about 99% and the heat of reaction could be recovered. The load on the second reactor was as small as about 1% and the ethylene concentration after liquefaction of EDC was about 25%, thus recovery by absorption was easy.

EXAMPLE 4

The reaction was conducted in the same manner as in Example 1 except that chlorine was fed at a flow rate of 500 kg/hr, the oxygen content in the chlorine was 1.5%, and ethylene was supplied at a flow rate of 207 kg/hr with an excess of about 5% based on the chlorine. When the reaction temperature and the condensation temperature were maintained at 130° C. and 120° C., respectively, and the EDC vapor pressure at the condensation temperature was 2.7 atm against the total pressure of 3.7 atm, the components discharged as uncondensed gases were about 2,300 Nl/hr of oxygen, about 7,800 Nl/hr of ethylene, about 36,000 Nl/hr of EDC and about 1,500 Nl/hr of other gases. This composition was within the safety region shown in FIG. 2. The total volume of discharge gases was about 47,000 Nl/hr. The ethylene load on the second reactor was about 5% of the total load and the ethylene concentration after liquefaction of EDC was about 70%, thus permitting easy recovery by absorption. The heat of reaction was efficiently recovered to the amount of 95%.

EXAMPLE 5

The reaction was conducted in the same manner as in Example 1 except that chlorine was fed at a rate of 800 kg/hr, the oxygen content in the chlorine was 2.0%, and ethylene was fed at a rate of 121 kg/hr. The excess percentage of ethylene was about 2%. When the reaction temperature and the condensation temperature were maintained at 120° C. and 95° C., respectively, and the EDC vapor pressure at the condensation temperature was 1.42 atm against the total pressure of 2.80 atm, the components discharged as uncondensed gases were about 1,900 Nl/hr of oxygen, about 1,900 Nl/hr of ethylene, about 4,200 Nl/hr of EDC and about 300 Nl/hr of other gases. This composition was within the safety region shown in FIG. 2. The total volume of discharge gas under the above conditions was about 8,300 Nl/hr. The load on the second reactor was as small as about 2% of the total ethylene load and the ethylene concentration after liquefaction of EDC was about 50%, thus permitting easy recovery by absorption. The heat of reaction was efficiently recovered to the amount of 98%.

COMPARATIVE EXAMPLE 1

The reaction was conducted in the same manner as in Example 1 except that the condensation temperature was set at 50° C. The EDC vapor pressure at 50° C. was 0.308 atm relative to the total pressure of 4.018 atm. To avoid the explosive composition, ethylene feed was set at 325 kg/hr, which represented an excess of about 35%. The components discharged as uncondensed gases were about 4,400 Nl/hr of oxygen, about 76,600 Nl/hr of ethylene, about 6,800 Nl/hr of EDC and about 200 Nl/hr of other gases. Thus, the discharge gas formed a composition within the safety region with a large excess of ethylene, as shown in FIG. 2, and accordingly such a composition was safe irrespective of dilution with EDC. The volume of discharge gas was about 88,000 Nl/hr, which was greater than in Example 1. Since the load on the second reactor was as high as 26% of the total ethylene load, the equipment size had to be increased as compared with the one for Example 1. Moreover, the recovery of heat produced by the high-temperature reaction in the first reactor was 74% of the total heat of reaction and this percentage was lower than the percentage that could be realized in accordance with Example 1.

COMPARATIVE EXAMPLE 2

The reaction was conducted in the same manner as in Example 1 except that the condensation temperature was set at 50° C. The EDC vapor pressure at this condensation temperature was 0.308 atm against the total pressure of 4.018 atm. To avoid the explosive composition, nitrogen gas was fed at a rate of about 72,200 Nl/hr. Under the above conditions, the components discharged as uncondensed gases were about 4,400 Nl/hr of oxygen, about 4,400 Nl/hr of ethylene, about 6,800 Nl/hr of EDC, about 72,200 Nl/hr of nitrogen and about 200 Nl/hr of other gases. This was within the safety region shown in FIG. 3, owing to dilution by nitrogen gas.

In the above operation, nitrogen pressurized to at least 4.018 atm had to be fed. Moreover, the volume of discharge gas was about 88,000 Nl/hr which was about twice as large as the volume in Example 1. The load on the second reactor was about 2% of the total ethylene load, which was the same as in Example 1, but since the ethylene concentration was as low as about 5%, absorption was much delayed as compared with Example 1 and, thus, recovery was difficult.

What we claim is:

1. A method for producing dichloroethane which comprises reacting ethylene and chlorine in a liquid reaction medium containing dichloroethane as a main component in a first reactor, recovering the reaction product in the form of a liquid, leading the discharge in the form of a discharge gas which contains unreacted ethylene from the first reactor to a second reactor where the unreacted ethylene is reacted with chlorine, and diluting said discharge gas which contains the unreacted ethylene and oxygen in a molar ratio of 3:97 to 90:10 with a dichloroethane vapor so that the content of dichloroethane in the resulting mixture is at least 15% by mole based on the mixture of ethylene, oxygen and dichloroethane, thereby preventing the unreacted ethylene and oxygen from forming an explosive gas mixture.

2. The method of claim 1, wherein said ethylene and chlorine are fed to the first reactor in an ethylene/chlorine ratio of 1.01:1.0 to 1.20:1.0 by mole, and oxygen is fed to the first reactor in an oxygen/chlorine ratio of 0.01:1.0 to 0.1 to 1.0 to mole.

3. The method of claim 1, wherein the content of oxygen in said resulting mixture is at most 40% by mole, and the ratio of oxygen to dichloroethane in said resulting mixture is not more than 3/2 by mole.

4. The method of claim 1, wherein the content of dichloroethane in said resulting mixture is at least 60% by mole.

5. The method of claim 1, wherein said reaction product is drawn out from the first reactor in the form of liquid and fed to a distillation column for purification, and a vapor containing a low-boiling fraction obtained from the top of said distillation column is introduced to a passage of said discharge gas.

6. The method of claim 1, wherein the reaction of ethylene and chlorine in the liquid reaction medium is carried out at a temperature of not less than the boiling point of dichloroethane, the liquid reaction medium is vaporized by the heat of said reaction and fed to a heat exchanger where a medium passed through the lower temperature side of the exchanger is maintained at a temperature of not less than 80° C. to thereby maintain a part of the vapor of liquid reaction medium uncondensed, a part of the condensed fraction is returned to the first reactor, while the remaining condensed fraction is taken out as the dichloroethane product, and the uncondensed fraction is sent to the second reactor in the form of a gas.

7. The method of claim 6, wherein the quantity of the uncondensed fraction of the liquid reaction medium vapor is from 0.05 to 1.0 mole per mole of the chlorine fed to the first reactor.

8. The method of claim 6, wherein the latent heat of condensation of the liquid reaction medium recovered by said heat exchanger is utilized as a heat source for a distillation column.

* * * * *

UNITED STATES PATENT AND TRADEMARK OFFICE
CERTIFICATE OF CORRECTION

PATENT NO. : 4,774,372

DATED : September 27, 1988

INVENTOR(S) : Shun WACHI et al

It is certified that error appears in the above-identified patent and that said Letters Patent is hereby corrected as shown below:

Column 4, line 25, "weight" should read --mole--.

Signed and Sealed this

Twenty-seventh Day of June, 1989

*Attest:*

DONALD J. QUIGG

*Attesting Officer*  *Commissioner of Patents and Trademarks*